United States Patent [19]
Williamson et al.

[11] 4,170,606
[45] Oct. 9, 1979

[54] SYNTHESIS OF ETHYLENE GLYCOL FROM CARBON MONOXIDE AND HYDROGEN USING AN IRIDIUM COMPLEX CATALYST AND A PYRIDINE BASE LIGAND

[75] Inventors: Roger C. Williamson, Allison Park; Thaddeus P. Kobylinski, Gibsonia, both of Pa.

[73] Assignee: Gulf Research and Development Company, Pittsburgh, Pa.

[21] Appl. No.: 894,173

[22] Filed: Apr. 6, 1978

[51] Int. Cl.$^2$ .................. C07C 27/06; C07C 29/00
[52] U.S. Cl. ..................... 260/449 L; 260/449 R; 260/449.5
[58] Field of Search .................. 260/449 R, 449 L

[56] References Cited

U.S. PATENT DOCUMENTS 3,940,432   2/1976   Walker et al. .................. 260/449 R

*Primary Examiner*—Howard T. Mars

[57] ABSTRACT

A process for selectively producing ethylene glycol which comprises contacting carbon monoxide and hydrogen with an iridium complex catalyst and a pyridine base ligand.

15 Claims, No Drawings

SYNTHESIS OF ETHYLENE GLYCOL FROM CARBON MONOXIDE AND HYDROGEN USING AN IRIDIUM COMPLEX CATALYST AND A PYRIDINE BASE LIGAND

BACKGROUND OF THE INVENTION

1. Field of the Invention

Ethylene glycol is the simplest and most important of the glycols which are widely used for many purposes and applications in industry. For example, ethylene glycol is a valuable component in antifreeze solutions for automobile engines, aircraft engines, ice-cream plants, and brewery cooling systems. Additionally, ethylene glycol finds widespread application in moistening and softening tobacco, cellophane, glue, gelatin, casein, paper and textile fibers, as well as solvents for dyes, printing inks, essential oils and various gums and resins. Similarly, ethylene glycol derivatives are important as emulsifying agents, plasticizers and explosives. Ethylene glycol was first synthesized by Wurtz in 1859, but, from a commercial standpoint, did not become important until 1925 when it was produced in large quantities via the of ethylene ofethylene oxide.

The iridium complex catalysts, as disclosed herein, exhibit superior hydrocarbon synthesis characteristics and selectivity to ethylene glycol formation when contacted with carbon monoxide and hydrogen under reaction conditions.

2. Description of the Prior Art

The reaction of carbon monoxide and hydrogen to produce monohydric and polyhydric alcohols is appreciated and disclosed by the prior art. Generally, however, most known processes produce a undesirably large mixture of alcohols, aldehydes, ethers, ketones and carboxylic acids, in addition to the polyhydric alcohol.

For example U.S. Pat. No. 3,833,634, entitled "Manufacture of Polyfunctional Compounds", issued to Pruett et al, on Sept. 3, 1974 describes a process for the preparation of polyfunctional oxygen-containing compounds, such as ethylene glycol and its derivatives, which comprise reacting carbon monoxide with hydrogen in the presence of a rhodium complex catalyst. In particular, tetrairidium dodecacarbonyl is described as unsuitable for use in the production of polyfunctional products such as ethylene glycol by the reaction between carbon monoxide and hydrogen at increased temperature and pressure.

Another process is set forth in U.S. Pat. No. 3,940,432, entitled "Process for Making Ethylene Glycol", issued to Walker et al, on February 4, 1976 which relates to the production of ethylene glycol and methanol from carbobn monoxide and hydrogen, wherein said carbon monoxide and hydrogen are reacted in the presence of a metal carbonyl catalyst at elevated pressures and temperatures. Particularly, carbon monoxide and hydrogen are contacted with rhodium carbonyl cluster ions which can be associated with a counterion which may be rhodium per se, hydrogen, ammonia or any monovalent or polyvalent metal such as sodium, potassium, etc., the rarer earth metals of Group VIII metals of the periodic table, for example, iridium.

SUMMARY OF THE INVENTION

The present invention relates to a process for selective formation of ethylene glycol from carbon monoxide and hydrogen in the presence of a catalyst, which comprises contacting carbon monoxide and hydrogen with a catalytic amount of an iridium complex catalyst having the formula:

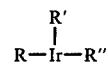

wherein R, R' and R" are either alike or different members selected from the group consisting of carbonyl radicals, hydrocarbonyl radicals, hydroxy radicals, acetylacetonate radicals and mixtures thereof; and a pyridine base ligand under reaction conditions.

DESCRIPTION OF THE INVENTION

The present invention relates to a process for the formation of ethylene glycol from carbon monoxide and hydrogen which comprises contacting said carbon monoxide and hydrogen with an iridium complex catalyst, a pyridine base ligand and optionally a solvent under reaction conditions for a time period sufficient to produce a product predominating in ethylene glycol. Although carbon monoxide and hydrogen are employed herein for reaction to produce ethylene glycol, it is understood that any combination of compounds that will form carbon monoxide and hydrogen in the reaction zone can also be used, for example, mixtures of hydrogen and carbon dioxide, water and carbon monoxide, etc.

The mixture of carbon monoxide and hydrogen used herein can be produced from anything containing carbon and hydrogen. Two types of reactions, for example, can be used for the production of synthesis gas; partial oxidation and steam reforming. Steam reforming is the more important process when natural gas (methane) is the hydrogen-carbon source. Partial oxidation is used primarily for heavy fuel and residue. The relative amounts of carbon monoxide and hydrogen present in the reaction mixture can be varied over a wide range. However, in general, the molar ratio range of carbon monoxide to hydrogen is from about 10:1 to about 1:10, especially from about 3:1 to about 1:3; however, conventional synthesis gas (mixtures of carbon monoxide to hydrogen) with a ratio of about 1:1 is convenient and satisfactory for the process herein. It is to be noted that molar ratios outside the aforestated ratio ranges can be employed and, as pointed out hereinabove, compounds or reaction mixtures which give rise to the formation of carbon monoxide and hydrogen under the reaction conditions defined herein can be used instead of mixtures comprising hydrogen and carbon monoxide which are used in the preferred embodiments of this invention.

Examples of iridium complex catalysts suitable for use herein include iridium dicarbonyl acetylacetonate, iridium tris(acetylacetonate) and iridium trihydroxide. The concentration of iridium complex catalyst used will depend upon the amount of product desired. Normally, the iridium complex catalyst is added to the reaction vessel at a concentration of form about $1 \times 10^{-6}$ gm moles/liter to about 1 gm mole/liter, preferably from about $1 \times 10^{-4}$ gm moles/liter to about $3 \times 10^{-2}$ gm moles/liter, based upon the reaction mixture.

It is to be noted that the iridium complex catalysts herein when contacted with carbon monoxide and hydrogen under reaction conditions will selectively produce ethylene glycol; however it is necessary to add a ligand to the reaction mixture to expedite ethylene glycol formation. Ligands which are suitable for use herein include pyridine base ligands, and include 2-hydroxypyridine, 2-aminopyridine, 2-(dimethylamino) pyridine, and the like. The iridium complex and ligand catalyst are normally used at a molar concentration of from about 1:1 to about 1:10, especially from about 1:1 to about 1:5.

In a preferred mode, carbon monoxide, hydrogen, iridium complex catalyst and pyridine base ligand, as described herein, are mixed with a solvent and introduced into a pressure-resistant reaction vessel, for example, a stainless steel autoclave with agitation means. Agitation is defined herein as shaking, rocking, stirring, percolation with synthesis gas, etc. Carbon monoxide and hydrogen can conveniently be converted into ethylene glycol in a batch operation or in a continuous process. When the batch method is used carbon monoxide, hydrogen, iridium complex catalyst and a pyridine base ligand mixed with a solvent are introduced into the reaction vessel and the pressure and temperature are adjusted to the operating reaction conditions. If the system is a closed system, the pressure is raised to the desired level with carbon monoxide and hydrogen before the reaction is initiated and the pressure falls as the reaction proceeds, but never below reaction pressure. Alternatively, the system can be equipped with a reservoir which contains synthesis gas and which feeds said gas to the reaction vessel at a set pressure on demand, thus maintaining a particular pressure level.

Solvents which are suitable for use herein include any inert solvents that will maintain the reaction mixture in solution, including alcohols, ethers, paraffins and aromatics. Illustrative of the solvents which are generally suitable in the practice of the invention herein include, for example, alcohols, such as methanol, ethanol, propanol, etc., ethers, such as tetrahydrofuran, tetrahydropyran, diethyl ether, 1,2-dimethoxybenzene, etc.; paraffins, such as propane, butane, hexane, etc.; and aromatics such as naphtha, kerosene, mineral oil and the like. It is to be noted that the use of solvents is desirable to promote uniform contact of the carbon monoxide, hydrogen and catalyst. When a solvent is utilized, the various components in the reaction medium, such as catalyst and ligand, can completely dissolve therein, or they can partially dissolve and form a slurry. Generally, the iridium complex catalyst and solvent (when used) are used in a molar ratio of from about 1:10 to about 10:1, especially from about 1:5 to about 5:1.

In a preferred continuous process for producing ethylene glycol; carbon monoxide, hydrogen, an iridium complex catalyst, a pyridine base ligand and optionally a solvent or slurry medium are continuously fed into a pressure-resistant vessel as described herein at a constant rate. The above mixture is next reacted under reaction conditions for a time period sufficient to selectively produce ethylene glycol. It is to be noted that lesser amounts of methanol and other by-products are produced along with the ethylene glycol.

Pressures which are suitable for use in our process generally are above about 10,000 psig (68.30 MPa), but should not be in excess of about 50,000 psig (341.50 MPa). An especially desirable pressure range is from about 15,000 psig (102.45 MPa) to about 40,000 psig (273.20 MPa), preferably about 20,000 psig (136.60 MPa) to about 30,000 psig (204.90 MPa). Temperatures which are suitable for use in our process are those temperatures which initiate a reaction between the reactants herein to selectively produce ethylene glycol, generally from about 100° C. to about 600° C., preferably from about 180° C. to about 300° C. The reaction is conducted for a time period sufficient to selectively convert carbon monoxide and hydrogen to ethylene glycol, normally from about 0.5 hour to about 10 hours, especially from about 1 hour to about 5 hours. Recovery of the desired ethylene glycol from the reaction product can be effected in any convenient or conventional manner, for example, by distillation. It should be noted that at ambient pressure (atmospheric pressure) and 197.2° C., the ethylene glycol will distill off.

DESCRIPTION OF PREFERRED EMBODIMENTS

The reactions herein were performed in a stainless steel, pressure-resistant, 300 cc. type 316 autoclave marketed commercially by Autoclave Engineers. In Example I, carbon monoxide, hydrogen, ligand, and iridium complex catalyst mixed with a solvent were introduced into the autoclave. The autoclave was connected to another larger reservoir containing synthesis gas (hydrogen to carbon monoxide molar ratio of 1:1), which fed said synthesis gas into the steel autoclave at a set pressure on demand. Thus, the reactor pressure was maintained throughout the course of the reaction. The reaction pressure and temperature were adjusted to operating conditions and the mixture reacted for a period of time sufficient to produce ethylene glycol.

The following Examples serve to further illustrate and instruct one skilled in the art the best mode of how to practice this invention and are not intended to be limiting thereof.

EXAMPLE I

Into a 300 cc. stainless steel type 316 autoclave, marketed commercially by Autoclave Engineers, were charged 1.00 gm of iridium dicarbonyl acetylacetonate and 1.0 gm of 2-hydroxy pyridine dissolved in 100 cc. of 1-propanol. The reactor was next purged twice with nitrogen gas, once with synthesis gas to remove oxygen therefrom and then pressurized to 15,000 psig (103.4 MPa) with synthesis gas. The temperature of the autoclave was then increased to 230° C. and the pressure was adjusted to a working pressure of about 25,000 psig (172.4 MPa). The reaction was allowed to proceed for approximately seven hours, after which the reactor was cooled by an internal cooling coil to about −75° C.

The reactor was vented through a dry gas meter, a gas sample was taken for a mass spectral analysis, and the liquid product was analyzed using a Model 900 Perkins-Elmer gas chromatograph utilizing a 16 ft. (4.88 meters) × ⅛ in. (0.32 centimeter) stainless steel column wherein 8 ft. (2.44 meters) of the column was packed with 80/100 mesh Poropak Q and other 8 ft. (2.44 meters) was packed with 80/100 Poropak R. Poropak Q and Poropak R are a form of polyvinyl benzene marketed commerically by Waters Associates, a corporation located in Milford, Massachusetts. The gas chromatograph was programmed to increase from 40° C. to 190° C. at a rate of 32° C./min and with a helium flow rate of 30 cc/min.

An analysis indicated that 20 gms of product was produced with the following mole percent selectivity:

| Compound | Selectivity, Mole % |
| --- | --- |
| Ethylene Glycol | 43.5 |
| Methanol | 30 |

| Compound | Selectivity, Mole % |
| --- | --- |
| Water | trace |
| Methylformate | trace |
| Propylformate | 26 |

It is to be noted that the reaction produced a molar ratio of ethylene glycol to methanol of 1.45:1, calculated as moles ethylene glycol/moles of methanol. We believe that by varying the parameters in this Example I, in accordance with the dictates herein, the product produced will contain molar ratios of ethylene glycol to methanol in the range of from about 0.6:1 to about 6:1, generally from about 1:1 to about 3:1.

EXAMPLE II

The procedure of Example I was followed with the following exceptions: rhodium dicarbonyl acetylacetonate was substituted for the iridium dicarbonyl acetylacetonate and the reaction was conducted for four hours.

An analysis indicated that 25 grams of product was produced with the following mole percent selectivity:

| Compound | Selectivity, mole % |
| --- | --- |
| Ethylene Glycol | 13 |
| Methanol | 59 |
| Water | trace |
| Methyl Formate | 3 |
| Propyl Formate | 24 |

The molar ratio of ethylene glycol to methanol produced was only 0:22:1.00 calculated as moles of ethylene glycol/moles of methanol. The above Example II is for comparative purposes only and does not form a part of this invention.

Obviously, many modifications and variations of the invention, as hereinabove set forth, can be made without departing from the spirit and scope thereof, and therefore only such limitations should be imposed as are indicated in the appended claims.

We claim:

1. In a process for the selective production of ethylene glycol from carbon monoxide and hydrogen in the presence of a catalyst, the improvement which comprises contacting carbon monoxide and hydrogen with a catalyst consisting essentially of a catalytic amount of an iridium complex catalyst selected from the group consisting of iridium dicarbonyl acetyl acetonate, iridium tris(acetylacetonate) and mixtures thereof and a pyridine base ligand; wherein the carbon monoxide and hydrogen are in a molar ratio of from about 1:10 to about 10:1; the iridium complex catalyst concentration is from about $1 \times 10^{-6}$ gm. moles/liter to about 1 gm. mole/liter based on the reaction mixture; the iridium complex catalyst and ligand are in a molar ratio of from about 1:1 to about 1:10; having a pressure of from about 10,000 psig. (68.30 MPa) to about 50,000 psig. (341.50 MPa), and a temperature of from about 180° C. to about 300° C., for a period of time sufficient to produce ethylene glycol.

2. The process according to claim 1 wherein the carbon monoxide and hydrogen are in a molar ratio of from about 1:3 to about 3:1.

3. The process of claim 1 wherein the iridium complex catalyst is iridium dicarbonyl acetylacetonate.

4. The process of claim 1 wherein the iridium complex catalyst concentration is from about $3 \times 10^{4}$ gm moles/liter to about $3 \times 10^{-2}$ gm moles/liter based on the reaction mixture.

5. The process of claim 1 wherein the ligand selected from the group consisting of 2-hydroxypyridine, 2-aminopyridine, or 2(methylamino)pyridine and mixtures thereof.

6. The process according to claim 1 wherein the ligand is 2-hydroxypyridine.

7. The process of claim 1 wherein the iridium complex catalyst and ligand are in a molar ratio of from about 1:1 to about 1:5.

8. The process according to claim 1 including a solvent selected from the group consisting of alcohols, ethers, paraffins or aromatics and mixtures thereof.

9. The process according to claim 8 wherein the solvent is propanol.

10. The process of claim 8 wherein the iridium complex catalyst and solvent are in a molar ratio of from about 1:10 to about 10:1.

11. The process of claim 8 wherein the iridium complex catalyst and solvent are in a molar ratio of from about 1:5 to about 5:1.

12. The process according to claim 1 having a pressure of from about 20,000 psig (136.60 MPa) to about 30,000 psig (204.90 MPa).

13. The process of claim 1 having a temperature of from about 100° C. to about 600° C.

14. The process according to claim 1 having a reaction time period of from about 0.5 hour to about 10 hours.

15. The process according to claim 1 having a reaction time period of from about 1 hour to about 5 hours.

* * * * *